US00PP22047P2

(12) United States Plant Patent
Deuter

(10) Patent No.: US PP22,047 P2
(45) Date of Patent: Jul. 26, 2011

(54) ***MISCANTHUS* PLANT NAMED 'MBS 7002'**

(50) Latin Name: *Miscanthus*
Varietal Denomination: MBS 7002

(75) Inventor: Martin Deuter, Wanzleben (DE)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 12/387,429

(22) Filed: May 1, 2009

Related U.S. Application Data

(60) Provisional application No. 61/050,162, filed on May 2, 2008.

(51) Int. Cl.
*A01H 5/00* (2006.01)

(52) U.S. Cl. ..... Plt./384

(58) Field of Classification Search ..... Plt./384
See application file for complete search history.

(56) References Cited

OTHER PUBLICATIONS

Münnich, C., and Jakob, K. (Nov. 27, 2008). Miscanthus—Breeding at Tinplant for US market. Int. Miscanthus-Tagung vom.27.—Nov. 28, 2008 in der Schweiz (International Miscanthus meeting of Nov. 27-28, 2008, Switzerland) (File: poster_Nov2008.pdf).

Zhang, J. (Apr. 26-27, 2007) "Lignocellulosic Feedstock Improvement", at the "Fueling Change With Renewable Energy" symposium, University of Illinois at Urbana-Champaign (File: Zhang_Talk_2007.pdf).

"'Nagara' eine neue Miscanthus-Sorte für die Biomassegewinnung" ("Nagara, a new Miscanthus variety for biomass production"; Apr. 9, 2008) Tinplant Biotechnik und Pflanzenvermehrung GmbH, website (File: NagaraWebpage_Apr2008.pdf). Leaflet created in and distributed from Aug. 2007.

Gutterson, N. (Aug. 19, 2008) "Bottlenecks in Feedstock Production: Can Biotechnology Address These?", at the International Conference for on Sorghum for Biofuels, Aug. 19-22, 2008, Houston Texas; (File: Gutterson_Talk_2008.pdf).

Gutterson, N. (Jan. 17, 2008) "Plant Biotechnology and Cellulosic Ethanlo Production", at the "Second Decade of Crop Biotechnology" Farm Foundation Conference, Jan. 17-18, 2008, Washington, D.C.; (File: Gutterson_Talk2_2008. pdf).

Ivanic, R. (May 19, 2009) "Miscanthus Potential for Second Generation Biofuels", at the 2nd Generation Biofuels Symposium, West Lafayette, IN, May 19, 2009 (File: Ivanic_Talk_2009.pdf).

Allen, D. (Jan. 10, 2008) "Genetic Improvement at Mendel Biotechnology", at the 5th annual SRI Symposium "Miscanthus at the University of Illinois" (File: Allen_Talk_2008.pdf).

Pude, R. Miscanthus International Meeting in Trier, Germany (Nov. 7-8, 2006) www.miscanthus.de/texte/Pressebericht2006.htm (File: PressReleaseIntlMeeting.pdf). Nagara and Amuri varieties introduced, order forms distributed.

*Primary Examiner* — Susan B McCormick Ewoldt
(74) *Attorney, Agent, or Firm* — Cooley LLP

(57) ABSTRACT

A new and distinct cultivar of *Miscanthus* plant named 'MBS 7002', characterized by its rigorous growth rate, plant height of about 2.7 meters, green-colored leaves, high biomass yield and high tiller density.

2 Drawing Sheets

Latin name of genus and species: *Miscanthus* spp.
Varietal denomination: 'MBS 7002'.

BACKGROUND

The present disclosure relates to a new and distinct cultivar of hybrid *Miscanthus* originated as a cross from *Miscanthus sacchariflorus* (♀, 4n)×*M. sinensis* (♂, 2n) plants and will be referred to hereafter by its cultivar name, 'MBS 7002.' 'MBS 7002' represents a new cultivar of *Miscanthus* species, a perennial grass which is grown for biomass production, landscape use and ornamental value.

'MBS 7002', also known as 'Lake Erie', was selected for its vigorous growth from a selection field which was established from seedlings. The seedlings were obtained from seeds of a polycross of *Miscanthus sacchariflorus* (♀, 4n) and *M. sinensis* (♂, 2n) plants. 'MBS 7002' was generated by crossing a single large-stemmed *M. sacchariflorus* genotype from Japan (accession No.: 93M0005064, ploidy: 4x) as a female parent with a population of 15 *M. sinensis* plants as pollen donors (accession Nos.: 93m0146002, 92M0179020, 92M0179017, 93M0147009, 92M0179016, 93m0146012, 93M0144001, 93m0146017, 92m0086, 92m0179015, 93m0146001, 93M0084, 93m0006005, 93M0006003, and 93m0007212; ploidy: 2x). From this cross, 158 seedlings were obtained and planted in a field. Based on field observations, one tetraploid variety having high biomass was selected and designated as 'MBS 7002'. 'MBS 7002' of the present application is 100% fertile, and is about 95% to 100% self incompatible, and 95% to 100% cross compatible. *Miscanthus* variety 'MBS 7001' disclosed in the co-pending U.S. Plant patent application Ser. No. 12/387,444 is an about 95% to 100% sterile genotype, and is almost completely self and cross incompatible.

'MBS 7002' is also difference from *Miscanthus* variety 'MBS 1002' disclosed in the co-pending application U.S. Plant patent application Ser. No. 12/584,496. 'MBS 1002' has higher seedling vigor upon transplanting, and during spring greenup, and has slightly better cold tolerance than 'MBS 7002'. They are siblings and recombine very well together in crossing.

The plant was established asexually from sterile rhizome buds in Klein-Wanzleben, Germany by the inventor. The shoot material was propagated on rooting media and the rooted plantlets were planted into pots in the greenhouse. The plants were planted into the field after one cold period. The characteristics of this cultivar have been determined to be stable and are reproduced true to type in successive generations.

SUMMARY

The following traits have been repeatedly observed and represent the characteristics of the new cultivar. The new cultivar 'MBS 7002' has not been observed under all possible environmental conditions. The phenotype may vary somewhat with variations in temperature, day-length, light intensity, soil types, and water and fertility levels without, however, any variance in genotype.

The following traits have been repeatedly observed and are determined the basic characteristics of 'MBS 7002', which in combination distinguish this *Miscanthus* hybrid from the known *Miscanthus*×*giganteus* and other ornamental *M. sinensis* forms. Plants for the botanical measurements in the present application are two and three-year-old plants. These plants would be considered as mature plants.

1. Vigorous growth
2. Top leaf height about 2.7 meters
3. Green leaves, no colored stripes are present
4. High biomass yield (about 20-30 tonnes per hectare)
5. High tiller density 'MBS 7002' can be distinguished from the *Miscanthus* cultivars Strictus (not patented), Super Stripe (U.S. Plant Pat. No. 18,161), Gold Bar (U.S. Plant Pat. No. 15,193), Little Zebra (U.S. Plant Pat. No. 13,008) and Mysterious Maiden (U.S. Plant Pat. No. 16,197) in that 'MBS 7002' has no stripes or colored bands on its leaves.

In side by side comparisons conducted in Klein-Wanzleben, Germany, 'MBS 7002' is more vigorous than either of its parent plants and produces more biomass than either parent. 'MBS 7002' has taller culms but demonstrates less lodging; hence it has stronger culms. The leaves stay longer on the culm compared to *M.*×*giganteus* and, therefore, the leaf loss during the winter is minimized which, in turn, leads to higher biomass yield.

The plant can be propagated by rhizomes, from meristem or nodes. This further distinguishes 'MBS 7002' from *M. sinensis* in that *M. sinensis* cannot be propagated by nodes. 'MBS 7002' develops inflorescences and viable seeds under optimal growing conditions.

BRIEF DESCRIPTION OF THE DRAWINGS

The accompanying color photographs illustrate the overall appearance and distinct characteristics of the new *Miscanthus* cultivar 'MBS 7002'.

The photograph in FIG. 1 was taken in Leamington, Ontario, Canada, and illustrates the overall growth habit and appearance of 'MBS 7002'.

Figure 1:
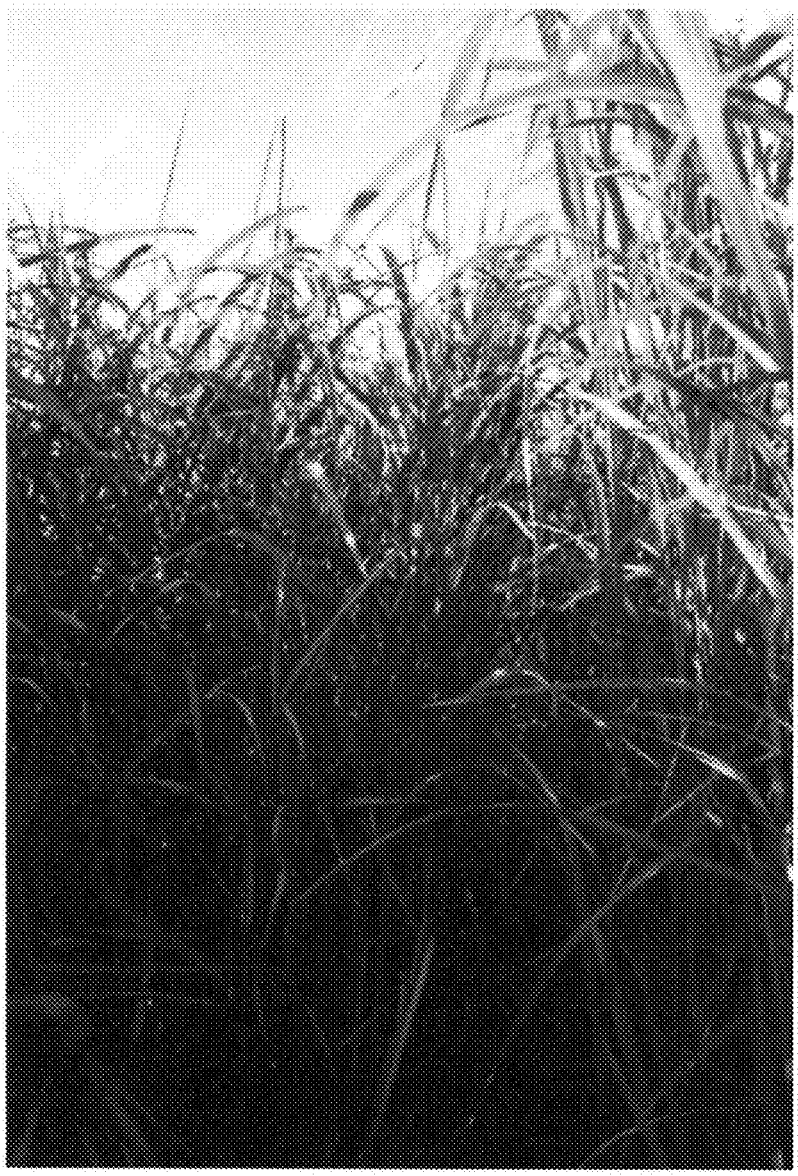
Figure 2:
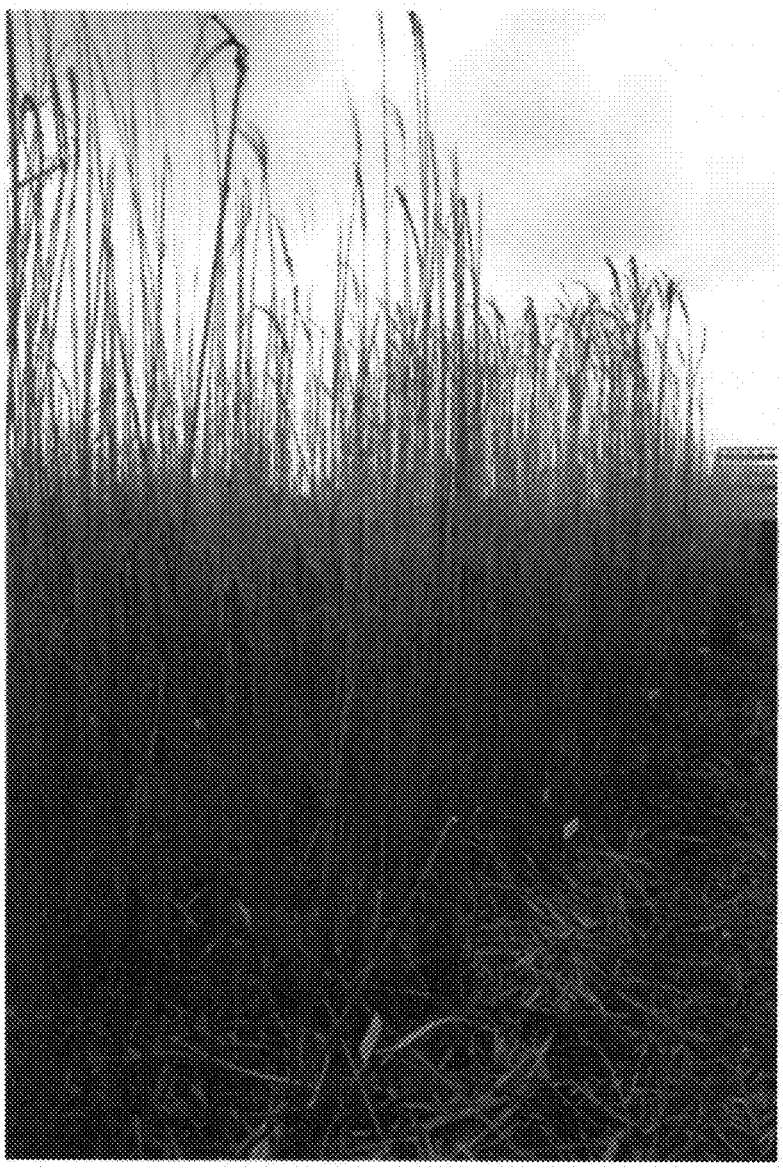

The photograph in FIG. 2 was taken in late fall, 2008 and illustrates the overall growth habit and appearance of 'MBS 7002' in Klein-Wanzleben, Germany as grown outdoors for 8 years. The 'MBS 7002' plants in the photo were harvested by removing above-ground biomass to above several inches above ground level every year for 7 years, and that the biomass visible in this photograph represents annual, rather than cumulative, growth.

DETAILED BOTANICAL DESCRIPTION OF THE PLANT

'MBS 7002' has not been observed under all possible environmental conditions, and the phenotype may vary significantly with variations in environment. The following observations, measurements, and comparison describe this plant as grown at Klein-Wanzleben, Germany, when grown in the field. All observations were recorded during the plant's dormant season (April 2008) and during the 2007 and 2008 growing season unless otherwise noted. The color determination is in accordance with the 1995 R.H.S. Colour Chart of The Royal Horticultural Society, London, England, except where general color terms of ordinary dictionary significance are used. Plants for the botanical measurements in the present application are two and three-year-old plants. These plants would be considered as mature plants.

Botanical classification: 'MBS 7002' is a fertile hybrid of a cross from *Miscanthus sinensis* and *Miscanthus sacchariflorus*.

Common name: Maiden grass.

Parentage: Polycross of *M. sacchariflorus* and several *M. sinensis*.

General description:

*Blooming period.*—'MBS 7002' may bloom in late fall in the southern and central U.S. Blooms are retained over the winter.

*Plant habit.*—Herbaceous, tuft forming, biomass grass with upright culms. 15-17 leaves per culm.

*Height and spread.*—Top leaf height about 2.7 meters.

*Hardiness.*—Productive growth in Klein-Wanzleben (north central), Germany and Ontario, Canada.

*Culture.*—Best in sandy loam, well-drained soil, higher yields at higher soil fertility.

*Diseases and pests.*—In United States 'MBS 7002' has shown excellent resistance to lesser stem borer spp. when compared to the public check variety *M. giganteus* cv. Illinois clone. Observations and confirmation on stem borer tolerance occurred during early growth stages within 2-8 weeks after field planting of seedling material. This has been observed across at least 7 locations, particularly in southeastern U.S.

*Root description.*—Fibrous, well branched and dense. Fast-developing creeping rhizomes, with shoots arising 5-10 cm from base of the culms. The tables 1 to 4 below provide average basal circumference, average compression circumference, average culm diameter, average culm length of 'MBS 7002', compared to *M.*×*giganteus*:

TABLE 1

Average Basal Circumference in cm*.

| Entry | Auburn, AL | Champaign, IL | Jerseyville, IL | Leland, MS | Starkville, MS | Entry Means |
|---|---|---|---|---|---|---|
| 'MBS 7002' | 97 | 83 | 76 | 103 | 78 | 87 |
| *M.* × *giganteus* 'Illinois' | 91 | 131 | 107 | 71 | 113 | 103 |
| Location Means | 96 | 98 | 87 | 91 | 93 | 93 |

*Data from 2 year old mature plants.

TABLE 2

Average Compression Circumference in cm*.

| Entry | Auburn, AL | Champaign, IL | Jerseyville, IL | Leland, MS |
|---|---|---|---|---|
| 'MBS 7002' | 33 | 29 | 34 | 18 |
| *M.* × *giganteus* 'Illinois' | 23 | 28 | 35 | 11 |
| Location | | | | |

TABLE 2-continued

| Average Compression Circumference in cm*. | | | | |
|---|---|---|---|---|
| Means | 35 | 29 | 35 | 15 |
| Entry | New Castle, KY | Providence Forge, VA | Starkville, MS | Entry Mean |
| 'MBS 7002' | 38 | 32 | 25 | 30 |
| *M.* × *giganteus* 'Illinois' | 36 | 31 | 25 | 27 |
| Location Means | 37 | 33 | 27 | 30 |

*Data from 2 year old mature plants

TABLE 3

| Average of Culm Diameter in cm*. | | | | |
|---|---|---|---|---|
| Entry | Auburn, AL | Champaign, IL | Jerseyville, IL | Leland, MS |
| 'MBS 7002' | 6.6 | 8.6 | 7.3 | 6.0 |
| *M.* × *giganteus* 'Illinois' | 5.7 | 8.4 | 8.2 | 5.9 |
| Location Means | 6.1 | 8.8 | 7.5 | 6.2 |
| Entry | New Castle, KY | Providence Forge, VA | Starkville, MS | Entry Mean |
| 'MBS 7002' | 7.2 | 6.6 | 4.7 | 6.7 |
| *M.* × *giganteus* 'Illinois' | 7.3 | 6.5 | 5.0 | 6.7 |
| Location Means | 7.2 | 6.6 | 5.2 | 6.8 |

*Data from 2 year old mature plants

TABLE 4

| Average of Culm Length (cm) | | | | |
|---|---|---|---|---|
| Entry | Auburn, AL | Champaign, IL | Jerseyville, IL | Leland, MS |
| 'MBS 7002' | 239 | 255 | 248 | 233 |
| *M.* × *giganteus* 'Illinois' | 193 | 291 | 283 | 172 |
| Location Means | 225 | 270 | 252 | 203 |
| Entry | New Castle, KY | Providence Forge, VA | Starkville, MS | Entry Mean |
| 'MBS 7002' | 261 | 268 | 201 | 244 |
| *M.* × *giganteus* 'Illinois' | 270 | 283 | 214 | 244 |
| Location Means | 255 | 265 | 199 | 238 |

*Data from 2 year old mature plants

Growth and propagation:

*Propagation.*—By culm division, in vitro culture, from rhizomes, meristem or auxilliary buds (nodes).

*Growth rate.*—Vigorous.

Culm (stem) description: (Plant ages for data below are from two and three-year-old plants. They would be considered mature plants.)

*General.*—Cylindrical, pithy, reed-like, erect, sheathed.

*Culm aspect.*—Rigid and held erect, none are cascading.

*Culm color* (*dormant season*).—Yellowish, lower internodes partly reddish. Midsummer color is green yellowish (RHS 144A-146B), lower internodes partly reddish orange (RHS 167B-167C), and vary with intensity depending on locations and growing conditions. The rate on which the culm color changes is dependent on location and growing conditions.

*Culm size.*—Average about 0.7 cm in diameter, culm circumference: 2.1 cm, and up to about 2.68 m in height.

*Basal circumference.*—193 cm.

*Compressed circumference.*—43.2 cm.

*Culm surface.*—Culm is covered with many hairs on the green leaf sheaths.

*Internode length.*—6 to 20 cm.

*Ligule.*—Membranous, about 4 mm (giganteus is 2.5-3 mm), color reddish, 145C, border 59D, longest hair is 2 mm (gig 1 mm), encircles the entire culm, inner surface is glabrous, hairs on the outer surface, long hairs are mainly on the side, hairs on the side are approximately 8 mm (gig 4-5 mm).

Foliage description:

*Leaf shape.*—Linear.

*Leaf base.*—Sheathed.

*Leaf division.*—Simple.

*Leaf apex.*—Acuminate.

*Leaf aspect.*—Emerging leaves are erect, blades are convex, leaf angle younger leaves 50°, leaf angle older leaves 5°, color code NN155B.

*Leaf tip younger leaves.*—½ pendently, meaning approximately half of the leaf tip area of the younger leaves bends downward.

*Leaf venation.*—Parallel, upper surface concave, lower surface convex.

*Leaf margins.*—Entire, visible, sharp short bristles under the microscope.

*Leaf size.*—Up to 100 cm, width: 2-3.2 cm.

*Leaf attachment.*—Sheathed.

*Leaf arrangement.*—Alternate, tapering.

*Leaf surface.*—Upper-light glossy, lower-matte, single hairs on some leaves on the lower surface.

*Leaf color* (*during growing season*).—Green, no stripes, range between 146A-147A.

Flower description:

*General description.*—Compact, fan-shaped panicle terminating from each culm in mid to late September, composed of numerous slender, silky aggregate racemes.

*Lastingness of inflorescence.*—Panicles are persistent from fall through winter.

*Fragrance.*—None.

*Panicle size.*—Average of 22 cm in length and 31 cm in width.

*Angle of raceme.*—30°.

*Panicle color.*—Varies from 152D-176B The intensity of these color grades depends on location and growing conditions. However, this color report indicates that 176B would be early panicle appearance and 152D is for mature panicle appearance.

*Spikelet description.*—Spikelet in pairs.

*Spikelet size.*—About 5 mm in length and 1 mm in width (excluding hairs).

*Spikelet color.*—152C.

*Spikelet hairs.*—12 mm in length, 158C in color.

*Awn size.*—1 mm.

Reproductive organ description:

*Androecium.*—Anthers; 3, 5 mm in length and 0.5 mm in width, red in color, 187B.

*Gynoecium.*—Stigma color is 187A, red, 4 mm in length and 0.5 mm in width.

*Caryopsis.*—Produces fertile seeds. 'MBS 7002' *miscanthus* has a small elliptical seed, which is a heavy anemochore with an average seed weight of 0.96 mg, a chamaephyte (buds permanently above ground) life form, with an annual seed production of 64-1200 seeds per plant depending upong pollen source availability. Healthy seed is clear amber to dark brown RHS167B-200A.

Yield: The average yield of 'MBS 7002' compared to *M.×gigantues* cv. 'Illinois' is shown below in Table 5 and Table 6.

TABLE 5

Average Yield (tons/ac) in Canada*

| Material Name | Leamington | Elora | Entry Mean |
|---|---|---|---|
| 'MBS 7002' | 2.6 | 5.3 | 3.9 |
| *M.* × *giganteus* 'Illinois' | 1.7 | 4.5 | 3.1 |
| Location Means | 2.4 | 6.1 | 4.3 |
| Lsd 0.05 | 1.3 | 2.8 | 1.8 |

*Data from 2 year old mature plants

TABLE 6

Average Yield (tons/ac) in U.S.*

| Material name | Auburn, AL | Champaign, IL | Providence Forge, VA | Leland, MS |
|---|---|---|---|---|
| 'MBS 7002' | 4.31 | 11.7 | 5.5 | 10.3 |
| *M.* × *giganteus* 'Illinois' | 2.56 | 13.6 | 5.3 | 4.7 |
| Location Means | 3.98 | 12.1 | 5.4 | 8.3 |
| LSD .05 | 2.6 | 3.1 | 1.3 | 3.8 |

| Material name | New Castle, KY | Jerseyville, IL | Starkville, MS | Mean |
|---|---|---|---|---|
| 'MBS 7002' | 10.3 | 3.8 | 4.7 | 7.2 |
| *M.* × *giganteus* 'Illinois' | 11.6 | 6.1 | 5.0 | 7.0 |
| Location Means | 10.8 | 5.1 | 4.5 | 7.2 |
| LSD .05 | 2.4 | 3.2 | 1.8 | 1.5 |

*Data from 2 year old mature plants

Moisture: The average moisture of 'MBS 7002' compared to *M.×gigantues* cv. 'Illinois' is shown below in Table 7 and Table 8.

TABLE 7

Average % Moisture comparisons in Canada*

| Material Name | Leamington | Elora | Entry Mean |
|---|---|---|---|
| 'MBS 7002' | 32 | 46 | 39 |
| *M.* × *giganteus* 'Illinois' | 36 | 48 | 42 |
| Location Means | 33 | 45 | 39 |
| Lsd 0.05 | 2.3 | 3.8 | 3.2 |

*Data from 2 year old mature plants

TABLE 8

2009 Average % Moisture content at harvest in U.S.*.

| Material name | Auburn, AL | Champaign, IL | Providence Forge, VA | Leland, MS |
|---|---|---|---|---|
| 'MBS 7002' | 20 | 32 | 21 | 18 |
| *M.* × *giganteus* 'Illinois' | 19 | 26 | 21 | 13 |
| Location Means | 19 | 30 | 22 | 17 |
| Lsd 0.05 | 1.1 | 2.3 | 2.4 | 3.4 |

| Material name | New Castle, KY | Jerseyville, IL | Starkville, MS | Entry Mean |
|---|---|---|---|---|
| 'MBS 7002' | 30 | 21 | 9 | 22 |
| *M.* × *giganteus* 'Illinois' | 30 | 11 | 12 | 19 |
| Location Means | 31 | 21 | 9 | 21 |
| Lsd 0.05 | 2.1 | 4.1 | 2.7 | 3.3 |

*Data from 2 year old mature plants

*M.×giganteus* is also a cross between *M. saccharafloris* (4x) and *M. sinensis* (2x) resulting in a sterile clone plant selection that is available to the public. This is how 'MBS 7002' was derived, only using different parentage in the ploycross as described. Therefore, *M.×giganteus* (3x) cv 'Illinois clone' is an excellent cultivar for comparison with 'MBS 7002'.

The invention claimed is:

1. A new and distinct cultivar of *Miscanthus* plant named 'MBS 7002' substantially as herein shown and described.

* * * * *

UNITED STATES PATENT AND TRADEMARK OFFICE

CERTIFICATE OF CORRECTION

PATENT NO. : PP22,047 P2
APPLICATION NO. : 12/387429
DATED : July 26, 2011
INVENTOR(S) : Martin Deuter It is certified that error appears in the above-identified patent and that said Letters Patent is hereby corrected as shown below:

Column 1 on line 1-5, please insert:

--CROSS-REFERENCE TO RELATED APPLICATION
This application claims priority to U.S. Provisional Patent Application Serial No. 61/050,162, filed on May 2, 2008, which is hereby incorporated by reference in its entirety.--

Signed and Sealed this
Fourth Day of October, 2011

David J. Kappos

David J. Kappos
*Director of the United States Patent and Trademark Office*